(12) United States Patent
Bommer et al.

(10) Patent No.: US 8,928,339 B2
(45) Date of Patent: Jan. 6, 2015

(54) METHODS AND SYSTEMS FOR AUTOMATED MEASUREMENT OF ELECTRICAL BONDS

(75) Inventors: Jason P. Bommer, Tacoma, WA (US); Andrew M. Robb, Ravensdale, WA (US); Stephen Lee Fahley, Renton, WA (US)

(73) Assignee: The Boeing Company, Chicago, IL (US)

( * ) Notice: Subject to any disclaimer, the term of this patent is extended or adjusted under 35 U.S.C. 154(b) by 437 days.

(21) Appl. No.: 12/915,642

(22) Filed: Oct. 29, 2010

(65) Prior Publication Data

US 2012/0105086 A1 May 3, 2012

(51) Int. Cl.
- *G01R 27/08* (2006.01)
- *G01N 27/04* (2006.01)
- *G01N 27/20* (2006.01)

(52) U.S. Cl.
CPC ............. *G01N 27/04* (2013.01); *G01N 27/20* (2013.01)
USPC .......... 324/713; 324/663; 324/714; 324/717; 324/718; 324/71.1

(58) Field of Classification Search
CPC ..................... H01L 2924/00; G01R 19/0092
USPC ................ 324/663, 713, 714, 717, 718, 71.1
See application file for complete search history.

(56) References Cited

U.S. PATENT DOCUMENTS

| | | | |
|---|---|---|---|
| 2,620,990 A * | 12/1952 | Cary et al. ................. 242/431 |
| 3,270,121 A * | 8/1966 | Pfeiffer ..................... 174/88 B |
| 3,599,095 A * | 8/1971 | Johnson .................... 324/718 |
| 6,384,610 B1 | 5/2002 | Wilson | |
| 6,693,417 B2 * | 2/2004 | Wilson .................... 204/228.7 |
| 6,776,859 B1 * | 8/2004 | Burke ........................ 156/64 |
| 6,889,568 B2 * | 5/2005 | Renken ..................... 73/866.1 |
| 6,911,828 B1 | 6/2005 | Brossia et al. | |
| 7,129,718 B2 * | 10/2006 | Ho et al. ................... 324/713 |
| 7,317,321 B2 | 1/2008 | Hilleary | |
| 7,576,966 B2 * | 8/2009 | Heeter ...................... 361/215 |
| 7,642,975 B2 * | 1/2010 | Brunks et al. ............. 343/705 |
| 7,755,370 B2 * | 7/2010 | Shie ......................... 324/713 |
| 7,855,549 B2 * | 12/2010 | Renken et al. ............ 324/750.3 |
| 2002/0047097 A1 * | 4/2002 | Nishiyama et al. ........ 250/559.4 |
| 2006/0017448 A1 * | 1/2006 | Chen et al. ................ 324/538 |
| 2007/0220743 A1 * | 9/2007 | Tsukamoto et al. ....... 29/831 |
| 2009/0128169 A1 * | 5/2009 | Fay et al. .................. 324/700 |
| 2010/0019785 A1 * | 1/2010 | Wang et al. ............... 324/696 |
| 2010/0052704 A1 * | 3/2010 | Fay et al. .................. 324/700 |
| 2010/0094566 A1 | 4/2010 | Grant et al. | |

* cited by examiner

*Primary Examiner* — Tung X Nguyen
*Assistant Examiner* — Giovanni Astacio-Oquendo
(74) *Attorney, Agent, or Firm* — Armstrong Teasdale LLP (57) ABSTRACT

A structure is described that includes a first faying surface, a second faying surface for creating an electrical bond with the first faying surface, and a sensor operatively placed proximate the first faying surface and the second faying surface. The sensor includes a current port for injecting a fixed current through the electrical bond, a voltage port for sensing a voltage across the electrical bond induced by the fixed current, a processing device programmed to determine a resistance of the electrical bond based on the fixed current and sensed voltage, and a wireless interface for transmitting at least one of the sensed voltage and the determined resistance to an external device.

20 Claims, 8 Drawing Sheets

METHODS AND SYSTEMS FOR AUTOMATED MEASUREMENT OF ELECTRICAL BONDS

BACKGROUND

The field of the disclosure relates generally to the inspection of electrical bonds associated with a platform, and more specifically, to methods and systems for automated measurement of electrical bonds.

Currently, an exhaustive and time consuming inspection technique is utilized by mechanics in the inspection of electrical bonds that requires the mechanics to make physical contact with structural and system electrical bonds. In certain manufacturing environments, for example an aircraft production environment, such inspection is required at hundreds of points. Currently, such inspections are estimated to take several days to complete, using a hand held ohm-meter.

More specifically, to accomplish the inspection as currently conducted, the mechanic carries a handheld instrument that includes two probes and a visual read out. By making physical contact with the bond in question using the two ohm-meter probes, a resistance associated with the bond is measured in ohms and displayed on a display associated with the ohm-meter. For each resistance measurement, the mechanic manually records the measurement the value on paper, before moving on to inspect the next bond. If there are any obstructions, such as coverings, fairings, insulation, or panels, the mechanic must first remove these so that physical contact can be made with the bond using the ohm-meter probes.

Because of the manual recording of data and direct contact requirement, the inspection process takes a long time to complete and is therefore costly. Removal of obstructions to access the part adds to the inspection time. Human error can also be introduced into the inspection process due to the manual recording of resistance measurements.

BRIEF DESCRIPTION

In one aspect, a structure is provided that includes a first faying surface, a second faying surface for creating an electrical bond with the first faying surface, and a sensor operatively placed proximate the first faying surface and the second faying surface. The sensor includes current ports for injecting a fixed current through the electrical bond, voltage ports for sensing a voltage across the electrical bond induced by the fixed current, a processing device programmed to determine a resistance of the electrical bond based on the fixed current and sensed voltage, and a wireless interface for transmitting at least one of the sensed voltage and determined resistance to an external device.

In another aspect, a method for configuring a structure for the testing of electrical bonds between two faying surfaces associated with the structure, is provided. The method includes operatively placing a sensor between a first faying surface and a second faying surface, the sensor including a current port for injecting a fixed current through the electrical bond and a voltage port for sensing a voltage across the electrical bond induced by the fixed current, and configuring the sensor to transmit at least one of the sensed voltage and a resistance calculated from the sensed voltage and fixed current upon receipt of an interrogation signal from an external source.

In still another aspect, a system for testing the integrity of electrical bonds between two faying surfaces is provided. The system includes a sensor operatively placed proximate the two faying surfaces comprising a current port for injecting a fixed current through the electrical bond, a voltage port for sensing a voltage across the electrical bond induced by the fixed current, and a wireless interface for transmitting at least one of the sensed voltage and determined resistance, the sensor configured to inject the fixed current upon receipt of a specific RF signal. The system further includes an interrogation device configured to output the specific RF signal and receive the transmission of the at least one of the sensed voltage and determined resistance from the sensor.

The features, functions, and advantages that have been discussed can be achieved independently in various embodiments or may be combined in yet other embodiments further details of which can be seen with reference to the following description and drawings.

DETAILED DESCRIPTION

In at least one aspect, the described embodiments relate to a sensor that enables fast and automated inspection of electrical bonds. In certain manufacturing and repair environments, utilization of such a sensor may reduce the time required to perform certain inspections by hundreds of hours. The sensor allows for wireless interrogation, for example by a mechanic, of the sensor from a distance. Interpretation of the data received from the interrogation allows for automatic assessment of the health of the bond. The embodiments provide for the interrogation and assessment without the need for direct contact of the bond and without any disassembly to remove obstructions between an interrogation device and the device to be interrogated. As further described below, in one embodiment the sensor combines a Kelvin double bridge circuit with wireless sensor and radio technology allowing for a relatively easy interrogation. In another embodiment, high precision instrumentation amplifiers are utilized along with supporting electronics to detect the low voltage associated with micro-ohm bonds, without the need for a Kelvin bridge.

Another embodiment of a sensor system described below includes an RF rectifier, a digital microcontroller, a current pulse generator, a precision instrumentation amplifier, and supporting electronics including power supply and wireless communication circuits. As described herein, one purpose of such a system is to measure the resistance of an aircraft bond joint or other electrical bond. In this embodiment, a known DC excitation current is passed through the bond joint and the voltage across the joint is sensed and quantified. The resistance of the joint is computed from the known excitation current and measured voltage. In embodiments, the sensor system is powered utilizing harvested RF energy. Therefore, the energy consumed by the sensor system should be minimized. Embodiments for minimizing energy consumption are also described. Specifically, energy consumption is minimized by carefully controlling the duty cycle of the sensor circuits, and limiting the duration of the excitation current to the shortest time possible.

Figure 1:
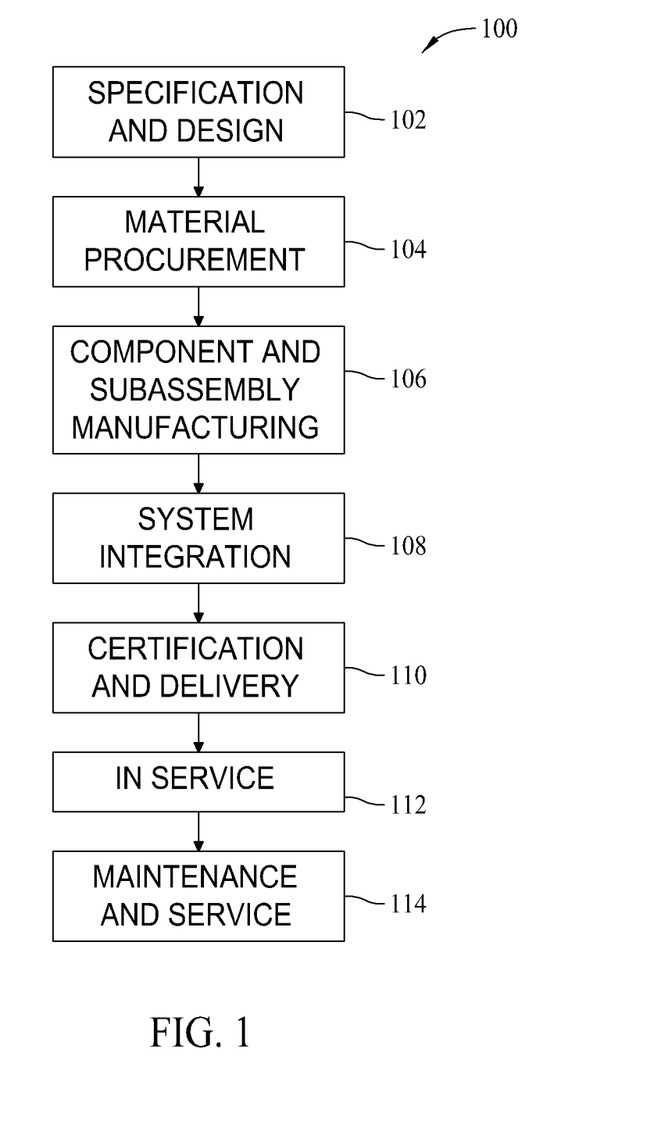
FIG. 1 is a flow diagram of an aircraft production and service methodology.
Figure 2:
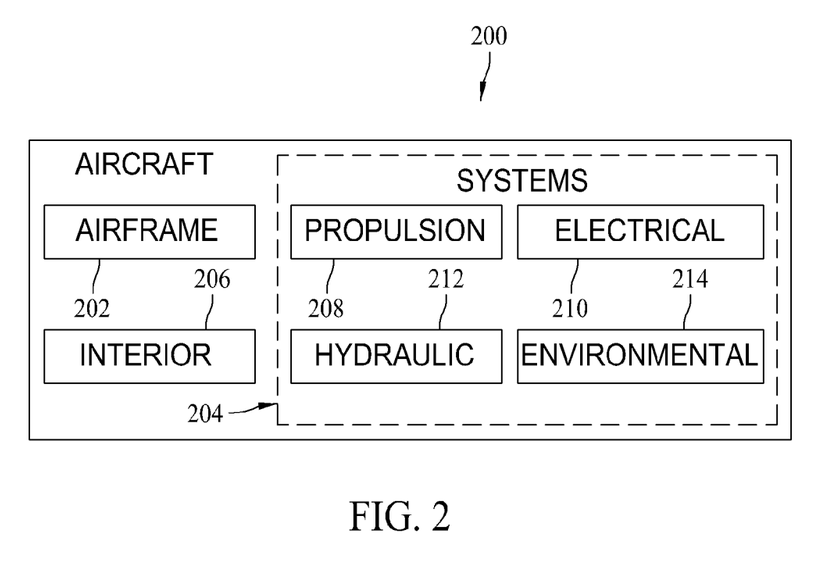
FIG. 2 is a block diagram of an aircraft.

Referring more particularly to the drawings, embodiments of the disclosure may be described in the context of aircraft manufacturing and service method 100 as shown in FIG. 1 and an aircraft 200 as shown in FIG. 2. During pre-production, aircraft manufacturing and service method 100 may include specification and design 102 of aircraft 200 and material procurement 104.

During production, component and subassembly manufacturing 106 and system integration 108 of aircraft 200 takes place. Thereafter, aircraft 200 may go through certification and delivery 110 in order to be placed in service 112. While in service by a customer, aircraft 200 is scheduled for routine maintenance and service 114 (which may also include modification, reconfiguration, refurbishment, and so on).

Each of the processes of aircraft manufacturing and service method 100 may be performed or carried out by a system integrator, a third party, and/or an operator (e.g., a customer). For the purposes of this description, a system integrator may include, without limitation, any number of aircraft manufacturers and major-system subcontractors; a third party may include, for example, without limitation, any number of venders, subcontractors, and suppliers; and an operator may be an airline, leasing company, military entity, service organization, and so on.

As shown in FIG. 2, aircraft 200 produced by aircraft manufacturing and service method 100 may include airframe 202 with a plurality of systems 204 and interior 206. Examples of systems 204 include one or more of propulsion system 208, electrical system 210, hydraulic system 212, and environmental system 214. Any number of other systems may be included in this example. Although an aerospace example is shown, the principles of the disclosure may be applied to other industries, such as the automotive industry.

Apparatus and methods embodied herein may be employed during any one or more of the stages of aircraft manufacturing and service method 100. For example, without limitation, components or subassemblies corresponding to component and subassembly manufacturing 106 may be fabricated or manufactured in a manner similar to components or subassemblies produced while aircraft 200 is in service.

Also, one or more apparatus embodiments, method embodiments, or a combination thereof may be utilized during component and subassembly manufacturing 106 and system integration 108, for example, without limitation, by substantially expediting assembly of or reducing the cost of aircraft 200. Similarly, one or more of apparatus embodiments, method embodiments, or a combination thereof may be utilized while aircraft 200 is in service, for example, without limitation, to maintenance and service 114 may be used during system integration 108 and/or maintenance and service 114 to determine whether parts may be connected and/or mated to each other.

The description of the different advantageous embodiments has been presented for purposes of illustration and description, and is not intended to be exhaustive or limited to the embodiments in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

Figure 3:
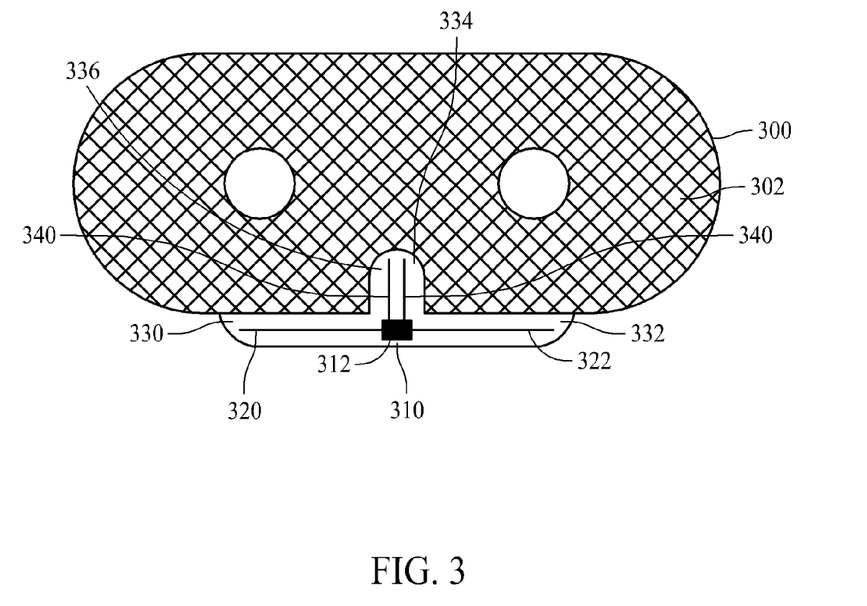
FIG. 3 is a top view of a thin metallic washer, having a main body and a sensor attached thereto.

FIG. 3 is a top view of a smartwasher 300 according to one embodiment. Smartwasher 300 is generally a thin metallic washer, having a main body 302, the smartwasher 300 including a sensor 310 attached thereto as further described. In the illustrated embodiment, smartwasher 300 is utilized for a faying surface bond. In one embodiment, sensor 310 incorporates an application specific integrated circuit (ASIC) 312 that includes a sensor, a transceiver, a power source and data storage. In embodiments, the power source incorporates one or more of RF energy harvesting, as described below, thermal gradient energy harvesting and piezoelectric energy harvesting. In the illustrated embodiment, a plurality of dipole legs 320, 322 form an antenna and extend from the ASIC 312 along a flexible dielectric 330 that extends from the main body 302. Flexible dielectric 330 includes two sections, an antenna carrier section 332 that is substantially adjacent a portion of a perimeter defined by body 302, and an attachment portion 334 which includes an upper member 336 and a lower member 338 (not shown in FIG. 3) which operate as a form of clip to attach the flexible dielectric 300 to the main body 302. A plurality of ports 340 are provided on each of the lower member and upper member 336 and are sometimes referred to herein as voltage ports and current ports.

In the illustrated embodiment, the flexible dielectric 330 serves as the sensor body for sensor 310 which houses all electronic components including antenna, the circuits described herein, and the voltage and current ports described below. The flexible dielectric 330 may be in any form and is attached to the body 302 of smartwasher 300 for convenience. The washer body 302 may not be utilized in all locations of a structure. Other embodiments are contemplated where a portion of an existing washer is set aside for current and voltage ports, and a protruding section (generally a dielectric) is used to house the electronics, to keep the electronics from being damaged between faying surfaces, and to prevent the antenna from being grounded out by the electrical bond between the faying surfaces. By connecting a flexible dielectric containing the circuits described herein to a washer, resulting in the "smartwasher" described herein, a step in assembly is eliminated since the installation where use of a smartwasher is contemplated generally utilizes a washer. Other installations my not utilize a washer. In such embodiments, a flexible or thin rigid dielectric may be installed between two faying surfaces. On this dielectric, the voltage and current ports contact the faying surfaces, and the described antenna and circuit will be placed on a portion of the flexible or thin rigid dielectric that protrudes away from the faying surfaces.

Figure 4:
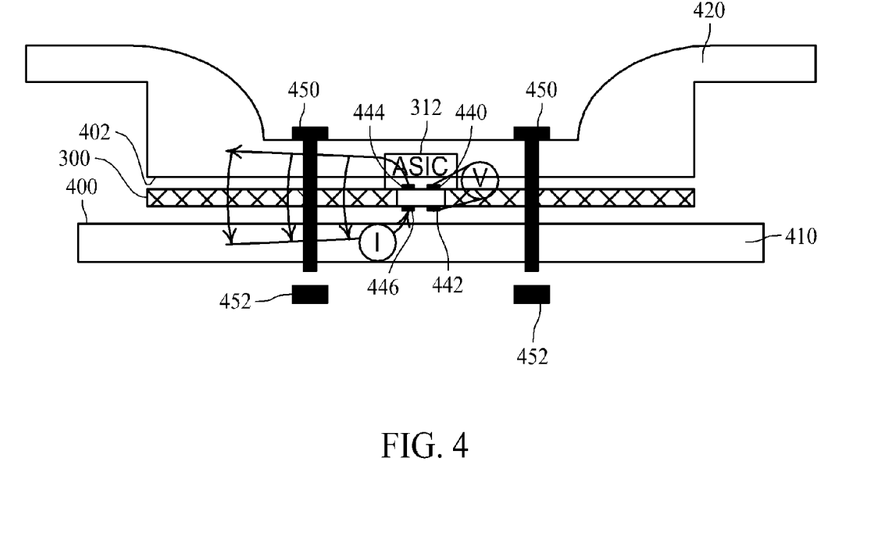
FIG. 4 is a cross-sectional view of the washer of FIG. 3 mounted between two faying surfaces.

FIG. 4 is a cross-sectional view of smart washer 300 mounted between two faying surfaces 400 and 402. Faying surface 400 is, for example, a portion of an airframe 410. Faying surface 402 is a portion of a bonding lug 420. In one embodiment, an electrical bond between faying surfaces 400 and 402 is desired to form a current return network. In a specific embodiment, the current return network is formed within an aircraft formed utilizing metallic components embedded throughout an otherwise composite airframe.

The voltage and current ports 340 are marked individually in FIG. 4 as contacts 440, 442, 444, and 446 that are situated on the upper member 336 and a lower member 338 to make contact with the respective faying surface 400 and 402. That contact is secured due to the bolts 450 and nuts 452 used to attach bonding lug 420 to airframe 410. As further explained herein, the measurement of the electrical bond is performed by determining a voltage across the voltage port (contacts 440 and 442) and determining a current that passes through current port (contacts 444 and 446). In alternative embodiments, multiple contacts may be associated with each port.

Figure 5:
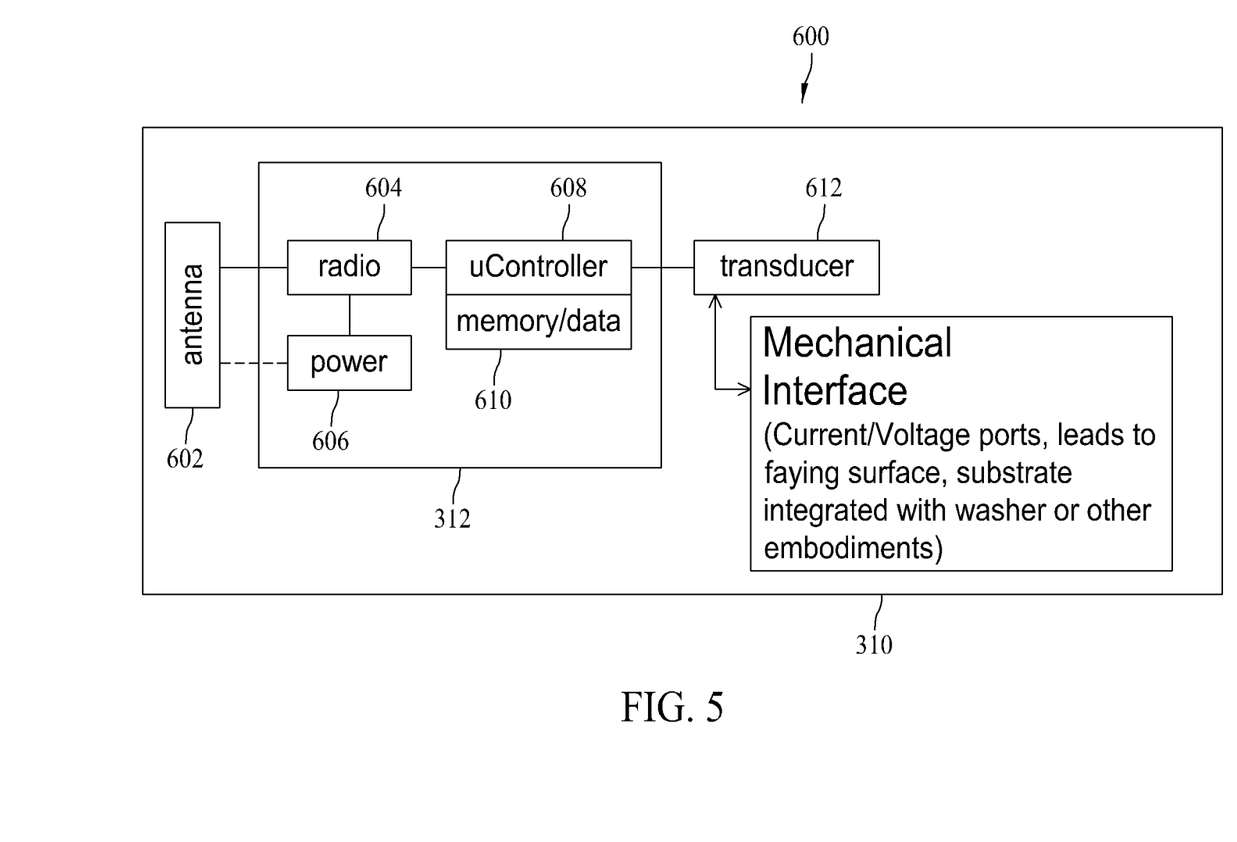
FIG. 5 is a block diagram of the sensor of FIGS. 3 and 4 further illustrating components of an application specific integrated circuit.

FIG. 5 is a block diagram 600 of sensor 310 that also further illustrates components of one embodiment of ASIC 312. Starting at antenna 602 (such as dipoles 320, 322), it provides an interface to radio 604 which, as described herein, operates as a transmitter and receiver. A portion of the power received at antenna 602 may be utilized to provide power to the remainder of ASIC 312 using a power module 606. Power module 606, in embodiments, includes a power storage capability.

The radio 604 is communicatively coupled to microcontroller 608 which is further coupled to a memory/data storage area 610. The microcontroller 608 is further coupled to a transducer 612, such as the Kelvin double bridge circuit or high precision instrumentation amplifier circuits mentioned above, which include a mechanical interface 614 to the faying surface. As described elsewhere herein, the mechanical interface 614 includes voltage and current ports and may be considered to include the dielectric to which the other components are coupled. The mechanical interface 614 may also be considered to include, for example, the capability for attachment to a washer, as described above. In one embodiment, microcontroller 608 may incorporate an analog to digital converter (ADC) utilized to measure the voltage at the voltage ports as further described herein. Generally, mechanical interface 614, and the components coupled thereto, provide a capability for determining the electrical resistance of the electrical bond between the airframe 410 and bonding lug 420.

Figure 6:
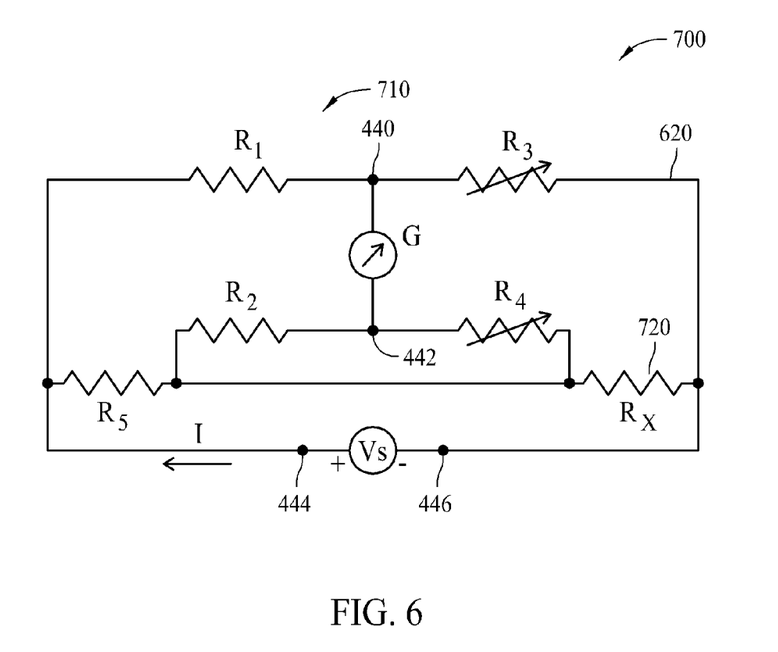
FIG. 6 is a schematic diagram of a micro-ohm meter sensor incorporating a Kelvin double bridge circuit.

More specifically, FIG. 6 is a schematic diagram 700 of one embodiment of micro-ohm meter sensor 620, particularly a Kelvin double bridge circuit 710 that may form the transducer 612 within ASIC 312 except for the bond resistance 720 that is associated with the bond in between airframe 410 and bonding lug 420. A Kelvin bridge can be used to detect very low resistances. Referring to schematic diagram 700, Rx represents the micro-ohm bond of the aircraft to be measured. Rs is a reference resistor that is comparable in value to the value or expected range of Rx. R3 and R4 are variable resistors, while R1 and R2 are fixed resistors. In use, R3 and R4 are adjusted until voltage (at G) is zero. At this point the balance condition exists, and the equation Rx/Rs=R4/R2=R3/R1 is satisfied, at which point Rx can be determined. To use the Kelvin bridge within transducer 612, those skilled in the art will understand that additional supporting circuitry is incorporated. The ports 440, 441, 444, and 446 are shown as nodes within the schematic 700. Utilization of the Kelvin double bridge circuit 710 allows for the injection of a fixed current into an electrical bond as well as we measurement of the voltage across the bond generated by the fixed current and the resistance of the bond.

Figure 7:
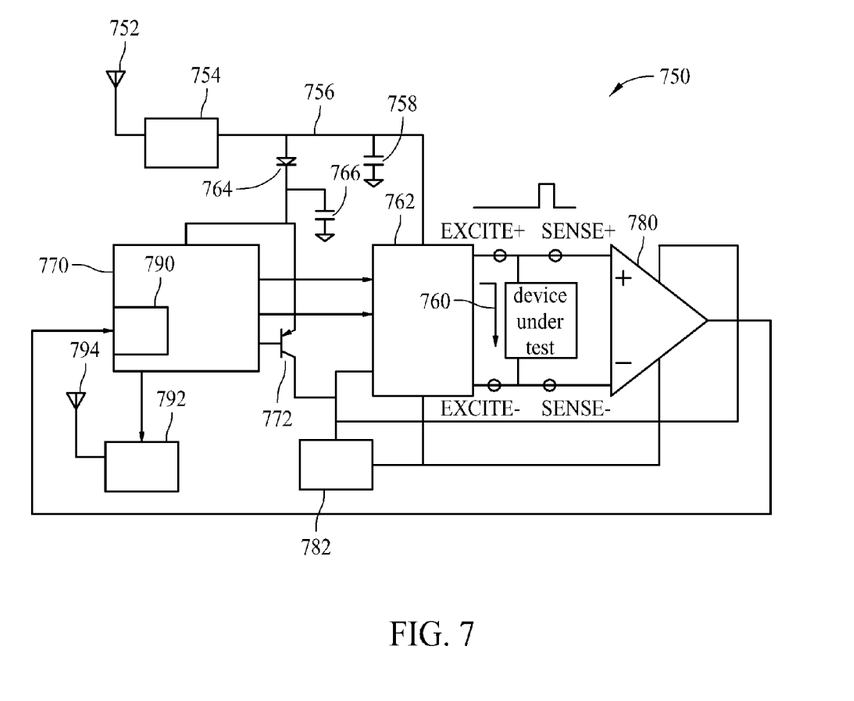
FIG. 7 is a schematic block diagram of one embodiment of a sensor system.

With reference to FIG. 7, a block diagram of a sensor system 750 is depicted. Sensor system 750, in the illustrated embodiment, is powered by energy harvested from wireless signals. As such, it does not utilize batteries which is advantageous for reasons described herein. Particularly, radio frequency (RF) energy is received by one or more receive antennas 752. A portion of the received RF energy is converted to DC power by an RF rectifier circuit 754. In this embodiment, the DC output signal 756 from the rectifier circuit 754 is referred to as VDET. This DC power is used to power the sensor system 750.

A portion of the DC energy is stored in one or more energy storage capacitors 758. This stored energy is used to generate a pulse of excitation current 760 in an exciter circuit 762. A smaller portion of the DC energy 756 supplied from the rectifier 754 is connected through a diode 764 to another capacitor 766 which supplies other circuits within sensor system 750. In this embodiment, the output of the diode 764 is referred to as VDD. A digital microcontroller 770 is powered directly from VDD. DC power is supplied from VDD through a PNP transistor switch 772 to create VCC. Operation of the transistor switch 772 is controlled by software in the microcontroller 770. The exciter 762, instrumentation amplifier 780, and charge pump circuits 782 are powered from VCC.

The charge pump circuits 782 generate a negative supply voltage referred to in the diagram as VEE. VEE is used to supply power to operational amplifiers (not shown) in the exciter 762 and to the instrument amplifier circuits. In this embodiment, when RF energy is received at the antenna 752, storage capacitors 758 and 766 begin to charge. When sufficient charge has built up on VCC, the microcontroller 770 starts up and monitors the voltage labeled as VDET. When sufficient charge has built up VDET, software in the microcontroller 770 executes a sensor measurement. To start a measurement, the microcontroller 770 turns the transistor switch 772 on, which turns on VCC and VEE. The instrumentation amplifier 780 and exciter circuits 762 contain high precision operational amplifiers for excellent DC measurement accuracy. These operational amplifiers have internal circuits that enhance DC accuracy but require some time at power up to achieve this accuracy. In order to achieve the desired accuracy, these circuits must be powered up for several hundred microseconds before a measurement is taken. In the illustrated embodiment, VCC is turned on for 640 microseconds before a measurement is started.

Figure 8:
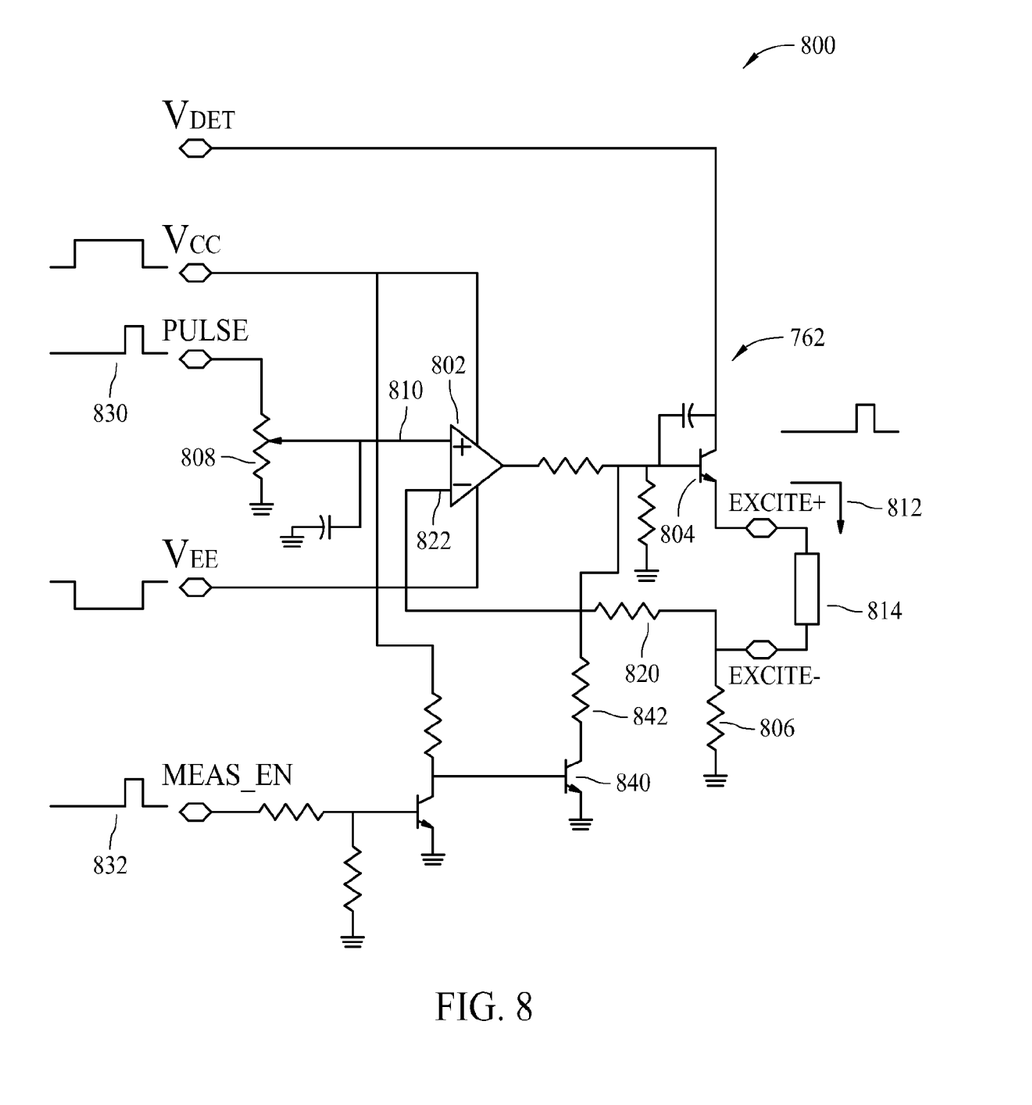
FIG. 8 is a circuit diagram of a current pulse generator utilized in the sensor system of FIG. 7.

FIG. 8 is a schematic 800 of the exciter circuit 762. The exciter circuit 762 includes an operational amplifier 802, a Darlington transistor 804, and a current sense resistor 806 configured in the form of a non-inverting voltage-to-current amplifier. In one embodiment, input signal PULSE is a nominal 1.2V. PULSE is divided using by a potentiometer 808 to 0.25V and applied to the + input 810 of the operational amplifier 802. Exciter current 812 is supplied to the device under test (DUT) 814 through the NPN Darlington transistor 804, which is controlled by the operational amplifier 802. The exciter current 812 passes through the DUT 814 and then through the sense resistor 806 to ground. DC feedback from the SENSE− terminal through a resistor 820 to the − input 822 of the operational amplifier 802 forces the voltage at SENSE− to equal the voltage at the + input 810 of the operational amplifier 802.

The voltage across the sense resistor 806 is therefore 0.25V. The current through the sense resistor 806, in the illustrated embodiment is therefore 0.25V/0.05 Ohms=5 Amperes. The current into the − input 822 of the operational amplifier 802 is virtually zero, and the excitation current 812 is therefore about five Amperes. The exciter circuit 762 is controlled by the PULSE signal 830 and the MEAS_EN signal 832. The MEAS_EN signal 832 is a gating signal that prevents the exciter 762 from injecting any current into the DUT 814 unless this signal is in a logic high state. This is necessary because during the amplifier startup time there are transient signals in the exciter 762 that would otherwise cause some of the stored energy in the VDET capacitor 758 (shown in FIG. 7) to discharge through the DUT 814, reducing the energy available for an excitation pulse 830.

When MEAS_EN signal 832 is at a logic low level, an NPN transistor 840 connected through a resistor 842 to the base of the Darlington transistor 804 is turned on. The voltage at the base of the Darlington transistor 804 is pulled close to ground and the Darlington transistor 804 cannot turn on. When the MEAS_EN signal 832 is in a logic high state, the exciter 762 generates a current pulse controlled by the PULSE signal 830. At about 640 microseconds after VCC is turned on, the PULSE and MEAS_EN signals 830, 832 are turned on, generating an excitation current of five Amperes. The DUT 814 is a resistance to be measured with a four terminal connection. Two connections are for the exciter current, EXCITE+, and EXCITE– (corresponding to the current ports), and the other two are for the voltage measurement SENSE+, and SENSE– (corresponding to the voltage ports).

SENSE+ and SENSE– are connected to the inputs of instrumentation amplifier 780 (shown in FIG. 7). The voltage between the SENSE+ and SENSE– connections is DC amplified and applied to the input of an analog-to-digital converter (ADC) 790 built into the microcontroller 770 (Both shown in FIG. 7). After allowing 150 microseconds for settling time in the exciter 762 and instrumentation amplifier 780 circuits, the microcontroller 770 reads the voltage from the ADC 790 and the measurement is complete. VCC, MEAS_EN 832, and PULSE 830 signals are turned off. The duration of the VCC on time is 800 microseconds, and the duration of the exciter pulse is 160 microseconds. In the embodiment shown, the sensor data is transmitted over a wireless link, via transmitter 792 and transmit antenna 794 to an external device such as a computer.

The above describe embodiments are therefore a portion of a system for measuring electrical bonds. In a typical fabrication scenario, sensors are acquired from stock, for example, in the form of smartwashers 300 or another embodiment as mentioned above. Whatever physical embodiment is utilized for a particular application, the sensors are essentially identical. When installed, each sensor 310 is assigned a unique identifier that includes, for example, an aircraft tail number and a location of the electrical bond on the aircraft. A reader is utilized in this programming, and as is easily imagined, a multitude of other applications exist outside of aircraft fabrication.

Once the device, such as a smartwasher 300 carrying sensor 310 is installed and deployed within a platform, in field data acquisition is performed, for example, using a reader that is operable to transmit an RF signal for powering the sensor 310 and retrieving data therefrom. A maintenance action decision is made based on the determined resistance in the electrical bond, for example, the reader is equipped with a processing device that is programmed to direct a maintenance action and record the event into a maintenance management system with which the reader communicates. An onboard maintenance management system is also contemplated. In such embodiments, sensor 310 includes an energy harvesting source that replenishes over time, and the processing device, such as ASIC 312, is programmed to take measurements at scheduled intervals and transmit those measurements to the onboard maintenance management system, for example, on the aircraft.

With the described embodiments, an entire electrical bond network can be scanned in a few hours. All electrical bonds that are not within the required tolerance are automatically flagged as dictated by the data management system. Using such generated data, which includes location data, a visual map of the entire bond network can be generated thereby providing quick access to displays of various data, status and progress of scanning. Examples of status and progress of scanning may include: progress of the inspection, completed scans vs. pending scans, date and time of the inspection, value at last inspection, history of all inspections, history of sensor, and next scheduled inspection.

This written description uses examples to disclose various embodiments, which include the best mode, to enable any person skilled in the art to practice those embodiments, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A structure comprising:
    a first faying surface;
    a second faying surface for creating a micro-ohm electrical bond with said first faying surface;
    a bolt coupling said first faying surface to said second faying surface to create the micro-ohm electrical bond between said first faying surface and said second faying surface, wherein said bolt is configured to create the micro-ohm electrical bond between said first faying surface and said second faying surface;
    a sensor operatively placed proximate said first faying surface and said second faying surface, said sensor configured to detect a level of voltage associated with the micro-ohm electrical bond between said first faying surface and said second faying surface, said sensor comprising:
        a current port for injecting a fixed current through the micro-ohm electrical bond, said current port comprising a first current contact that contacts said first faying surface and a second current contact that contacts said second faying surface;
        a voltage port for sensing a voltage across the micro-ohm electrical bond between said first faying surface and said second faying surface induced by the fixed current, said voltage port comprising a first voltage contact that contacts said first faying surface and a second voltage contact that contacts said second faying surface;
        a processing device programmed to determine a resistance of the micro-ohm electrical bond between said first faying surface and said second faying surface based on the fixed current and sensed voltage; and
        a wireless interface for transmitting at least one of the sensed voltage and the determined resistance to an external device.

2. The structure according to claim 1 further comprising a washer a portion of which is operable for placement between said first faying surface such that said washer is in contact with both said first and said second faying surfaces and said second faying surface, said sensor attached to said washer.

3. The structure according to claim 2 wherein said washer comprises:
    a metallic body; and
    a flexible dielectric extending from said metallic body, said sensor mounted on said flexible dielectric.

4. The structure according to claim 3 wherein said flexible dielectric comprises:
    an antenna carrier section substantially adjacent a portion of said metallic body; and
    an attachment portion comprising an upper member and a lower member operable to attach said flexible dielectric said metallic body.

5. The structure according to claim 1 further comprising a dielectric operable for placement between said first faying surface and said second faying surface, said sensor attached to said dielectric.

6. The structure according to claim 1 wherein said voltage port voltage contacts and said current port current contacts comprise a plurality of voltage and current contacts, respectively, for contacting said faying surfaces, wherein a plurality of first voltage contacts associated with said voltage port and a plurality of first current contacts associated with said current port are placed for engagement with said first faying surface, and a plurality of second voltage contacts associated with said voltage port and a plurality of second current contacts associated with said current port are placed for engagement with said second faying surface.

7. The structure according to claim 1 wherein said sensor comprises:
  a voltage measurement device for measuring the voltage across the electrical bond;
  a transceiver for transmitting the voltages measured at said voltage port; and
  at least one antenna for radiating the transmissions from said transceiver and receiving transmissions intended for said transceiver.

8. The structure according to claim 7 wherein said voltage measurement device comprises an analog to digital converter.

9. The structure according to claim 1 wherein said sensor comprises a storage device, said storage device operable for storing information related to a specific electrical bond location as received via said wireless interface.

10. The structure according to claim 1 wherein said sensor comprises a RF to DC converter for providing power to said sensor.

11. The structure according to claim 1 wherein said sensor comprises a Kelvin double bridge circuit, an electrical resistance associated with the electrical bond forming one resistance of the Kelvin double bridge circuit.

12. The structure according to claim 1 wherein said sensor comprises:
  an exciter circuit for outputting a fixed current through said current ports; and
  an instrumentation amplifier for sensing the voltage across said voltage ports.

13. A method for configuring a structure for the testing of micro-ohm electrical bonds between two faying surfaces associated with the structure, said method comprising:
  coupling a first faying surface to a second faying surface using a bolt to create a micro-ohm electrical bond, wherein the bolt is configured to create the micro-ohm electrical bond between the first faying surface and the second faying surface;
  operatively placing a sensor proximate the first faying surface and the second faying surface, wherein the sensor is configured to detect a level of voltage associated with the micro-ohm electrical bond between the first faying surface and the second faying surface, the sensor including a current port operatively placed between the first faying surface and the second faying surface for injecting a fixed current through the micro-ohm electrical bond between the first faying surface and the second faying surface, the current port including a first current contact that contacts the first faying surface and a second current contact that contacts the second faying surface, and a voltage port operatively placed between the first faying surface and the second faying surface for sensing a voltage across the micro-ohm electrical bond between the first faying surface and the second faying surface induced by the fixed current, the voltage port including a first voltage contact that contacts the first faying surface and a second voltage contact that contacts the second faying surface; and
  configuring the sensor to transmit at least one of the sensed voltage and a resistance calculated from the sensed voltage and fixed current upon receipt of an interrogation signal from an external source.

14. The method according to claim 13 wherein operatively placing a sensor proximate the first faying surface and the second faying surface comprises:
  configuring the current port such that a plurality of first current contacts of the current port are in contact with the first faying surface and a plurality of second current contacts of the current port are in contact with the second faying surface; and
  configuring the voltage port such that a plurality of first voltage contacts of the voltage port are in contact with the first faying surface and a plurality of second voltage contacts of the voltage port are in contact with the second faying surface.

15. The method according to claim 13 wherein operatively placing a sensor proximate a first faying surface and a second faying surface comprises attaching the sensor to a washer operable for placement between the first faying surface and the second faying surface such that the washer is in contact with both the first and second faying surfaces.

16. The method according to claim 15 wherein attaching the sensor to a washer comprises attaching a flexible dielectric on which the sensor is mounted to the washer such that the flexible dielectric extends from the washer.

17. The method according to claim 13 wherein operatively placing a sensor comprises attaching the sensor to a dielectric, a portion of the dielectric operable for placement between the first faying surface and the second faying surface.

18. The method according to claim 13 further comprising configuring the sensor to transmit a unique identifier including at least location information associated with the sensor.

19. A system for testing the integrity of micro-ohm electrical bonds between two faying surfaces, said system comprising:
  a bolt coupling said two faying surfaces to create the micro-ohm electrical bond, wherein said bolt is configured to create the micro-ohm electrical bond between said two faying surfaces;
  a sensor operatively placed proximate the two faying surfaces, said sensor configured to detect a level of voltage associated with said micro-ohm electrical bond between said two faying surfaces, said sensor comprising:
    a current port for injecting a fixed current through the micro-ohm electrical bond between said two faying surfaces, said current port comprising a first current contact that contacts a first of the faying surfaces and a second current contact that contacts a second of the faying surfaces;
    a voltage port for sensing a voltage across the micro-ohm electrical bond between said two faying surfaces induced by the fixed current, said voltage port comprising a first voltage contact that contacts the first of the faying surfaces and a second voltage contact that contacts the second of the faying surfaces;
    a processing device programmed to determine a resistance of the micro-ohm electrical bond between said two faying surfaces based on the fixed current and sensed voltage; and a wireless interface for transmitting at least one of the sensed voltage and determined resistance, said sensor configured to inject the fixed current upon receipt of a specific RF signal; and an interrogation device configured to output the specific RF signal and receive the transmission of the at least one of the sensed voltage and determined resistance from said sensor.

20. The system according to claim 19 wherein:

said current port comprises a plurality of first current contacts placed for contact with the first of the faying surfaces and a plurality of second current contacts placed for contact with the second of the faying surfaces; and said voltage port comprises a plurality of first voltage contacts placed for contact with the first of the faying surfaces and a plurality of second voltage contacts placed for contact with the second of the faying surfaces.

* * * * *